United States Patent [19]
Nakamura et al.

[11] Patent Number: 5,221,773
[45] Date of Patent: Jun. 22, 1993

[54] PROCESS FOR PURIFYING BORIC ACID FOR HYDROCARBON OXIDATION

[75] Inventors: Shinzo Nakamura, Sakai; Hiroyuki Ikushima, Tokyo; Yasuo Murakami; Noriyuki Ohira, both of Sakai, all of Japan

[73] Assignee: UBE Industries, Ltd., Yamaguchi, Japan

[21] Appl. No.: 922,547

[22] Filed: Jul. 31, 1992

[30] Foreign Application Priority Data

Aug. 2, 1991 [JP] Japan .................................. 3-280926

[51] Int. Cl.⁵ ............................................ C07C 29/00
[52] U.S. Cl. .................................................. 568/887
[58] Field of Search ................ 568/887, 836, 837, 1

[56] References Cited

U.S. PATENT DOCUMENTS

| | | | |
|---|---|---|---|
| 3,399,035 | 8/1968 | Broich et al. | 568/887 |
| 3,423,471 | 1/1969 | Golden et al. | 568/887 |
| 3,482,936 | 12/1969 | Russell | 568/887 |

FOREIGN PATENT DOCUMENTS 1498351  9/1967  France ................................ 568/887

*Primary Examiner*—Werren B. Lone
*Attorney, Agent, or Firm*—Finnegan, Henderson, Farabow, Garrett & Dunner

[57] ABSTRACT

CONSTRUCTION

The present invention relates to an industrial purification process in the process of manufacturing alcohols and ketones by oxidation of hydrocarbon wherein after removing by extraction organic impurities, formed as by-products of an oxidation reaction, from aqueous boric acid solution obtained by hydrolysis of an oxidation reaction solution containing boric acid ester, obtained by performing an oxidation reaction in the presence of boric acid, in order to essentially regenerate boric acid and prevent lowering of the reaction rate, selectivity and excessive soiling of the apparatus in the case of cyclically using said regenerated boric acid in an oxidation reaction, boric acid is regenerated and cyclically used again in said hydrocarbon oxidation reaction.

EFFECT

The present invention is a process for purifying boric acid for hydrocarbon oxidation which reduces the amount of harmful impurities to an extent that allows circulating aqueous boric acid solution to be reused in a continuing oxidation reaction, while also maintaining the selectivity of the oxidation reaction at a level of selectivity obtained with fresh boric acid.

18 Claims, 2 Drawing Sheets

PROCESS FOR PURIFYING BORIC ACID FOR HYDROCARBON OXIDATION

BACKGROUND OF THE INVENTION

The present invention relates to an industrial purification process in the process of manufacturing alcohols and ketones by oxidation of hydrocarbon wherein after removing by extraction organic impurities, formed as by-products of an oxidation reaction, from aqueous boric acid obtained by hydrolysis of an oxidation reaction solution containing boric ester, obtained by performing a hydrocarbon oxidation reaction in the presence of boric acid with gas containing molecular oxygen, using an organic polar solvent having an oxygen atom within its molecule, boric acid is regenerated and cyclically used again in said hydrocarbon oxidation reaction. As examples of usage of alcohols and ketones, in the case of cyclododecanol and cyclododecanone, they are used for the intermediate starting material of laurolactam, a monomer used in the manufacturing of 12-Nylon and for the starting material of a dodecane dibasic acid, and in the case of cyclohexanol and cyclohexanone, they are used for the intermediate starting material of caprolactam, a monomer used in the manufacturing of 6-Nylon and for the starting material of adipic acid.

Various methods of the prior art are known for purifying boric acid used in a process wherein boric acid that has been regenerated from aqueous boric acid, obtained by hydrolysis of an oxidation reaction solution obtained in a hydrocarbon oxidation reaction performed in the presence of boric acid, is used cyclically. Examples of known methods for purifying aqueous boric acid obtained by hydrolysis include steam stripping the aqueous boric acid obtained by hydrolysis of an oxidation reaction solution to remove organic impurities contained therein (see U.S. Pat. No. 3,423,571). However, the above-mentioned known steam stripping method has the disadvantage of being unable to remove a majority of the organic impurities, which have a detrimental effect on the oxidation reaction, even if a considerably large amount of steam is used.

In addition, examples of known methods wherein aqueous boric acid obtained by hydrolysis is purified with solvent include a method wherein aqueous boric acid obtained by hydrolysis is removed by extraction with saturated, linear or cyclic hydrocarbons such as cyclododecane, cyclohexane, cyclopentane, n-decane, n-heptane and n-hexane (see U.S. Pat. No. 3,679,751). However, as nearly all of the organic impurities contained in said aqueous boric acid are polar compounds, methods which use nonpolar solvents like the above-mentioned hydrocarbons for the extracting solvent have the disadvantage of being unable to achieve a satisfactory removal rate during removal of those impurities by extraction.

Moreover, examples of known methods wherein aqueous boric acid obtained by hydrolysis is crystallized include a method wherein boric acid crystals are removed from aqueous boric acid obtained by hydrolysis by crystallization, and organic impurities are removed by wet oxidation of the mother liquor formed as a result of said crystallization (see Japanese Patent Publication No. 4524/1977). This proposed method has the disadvantage of requiring high temperature and high pressure apparatus resulting in increased apparatus complexity and high equipment costs. In addition, another example of a known method wherein aqueous boric acid obtained by hydrolysis is crystallized is a crystallization purification method wherein only crystals obtained by removing boric acid crystals in the first stage of crystallization are cyclically used for an oxidation reaction as a result of two-stage crystallization from aqueous boric acid obtained by hydrolysis (see Japanese Patent Publication No. 39250/1970 and Japanese Unexamined Patent Publication No. 29299/1978). However, accumulation of organic substances is prevented by redissolving and returning the crystals obtained in the second stage of crystallization either to the first stage crystallization process or the hydrolysis process, and discarding a portion of the mother liquor of second stage crystallization while a portion of the second stage crystallization outside the system. Thus, this method has the disadvantage of being undesirable in terms of costs and the environment as a portion of the aqueous boric acid must be discarded. Thus, all of the methods of the prior art were not able to be satisfactory in terms of industrial use.

SUMMARY OF THE INVENTION

The object of the present invention is to provide a process for purifying an oxidation assistant wherein organic impurities contained in aqueous boric acid obtained by hydrolysis of an oxidation reaction solution, obtained in a hydrocarbon oxidation reaction, are removed in order to cyclically use boric acid, used in said hydrocarbon oxidation reaction, again in said oxidation reaction.

When manufacturing alcohols and ketones using a hydrocarbon oxidation reaction, it is known that the presence of boric acid is able to drastically increase the selectivity of the target alcohol and ketone products. However, as the occurrence of high-order oxidation cannot be completely prevented, organic impurities such as organic acids are constantly formed by the oxidation reaction resulting in the oxidation reaction solution containing a plurality of types of impurities.

The boric acid used in said oxidation reaction includes ortho- and meta-boric acid, $B_2O_3$ and $B_4O_5$ boric acid anhydrides or their mixtures.

As the formed alcohols and boric acid in the oxidation reaction solution are present as boric esters, when hydrolysis is performed to isolate the boric acid, an organic substance containing unreacted hydrocarbon, the alcohol and ketone of the target compound, and aqueous boric acid are obtained. The ortho-boric acid, meta-boric acid or anhydrous boric acid obtained by additional dehydration having a lower degree of hydration or their mixture that is obtained by removal of water from the aqueous boric acid are cyclically used again in the oxidation reaction. However, as organic impurities are distributed in this aqueous boric acid, if regenerated boric acid for which dehydration was performed to remove water from aqueous boric acid is used again in the oxidation reaction, adhesion of regenerated boric acid occurs in the reaction vessel. In addition, this also has the detrimental effect of remarkably reducing the efficiency of the oxidation reaction in terms of the conversion rate and selectivity of the alcohols and ketones. Thus, in order to industrially perform this oxidation reaction in the presence of boric acid, an industrial process is required wherein organic impurities in the boric acid to be reused cyclically are removed. As the various known technologies of the prior art have disadvantages as mentioned above, and as the industrial cyclic use of regenerated boric acid for performing an oxidation reaction remarkably decreases yield and is disadvantageous as a stable procedure with a high degree of selectivity while also having a considerable effect on economic feasibility, the inventors of the present invention invented process in order to solve these problems that allows aqueous boric acid obtained by isolation to be efficiently purified following hydrolysis of said oxidation reaction solution.

The present invention relates to a process for purifying boric acid for hydrocarbon oxidation wherein after removing by extraction organic impurities, formed as by-products of an oxidation reaction, from aqueous boric acid obtained by hydrolysis of an oxidation reaction solution, obtained in a hydrocarbon oxidation reaction performed in the presence of boric acid, using for said extraction an organic polar solvent having an oxygen atom within its molecule, boric acid is regenerated and used cyclically in said oxidation reaction.

In the case of removing by extraction organic impurities, formed as by-products of an oxidation reaction, from aqueous boric acid obtained by hydrolysis of an oxidation reaction solution using for said extraction an organic polar solvent having an oxygen atom within its molecule, a portion of the boric acid is dissolved in the resulting extraction solvent. However, by washing said extraction solvent with water and returning the resulting water containing boric acid to the extraction process using an organic polar solvent, the amount of boric acid lost can essentially be reduced to zero. This method may be performed by dividing between two extraction columns consisting of solvent extraction column 3 and water washing column 5 as illustrated in FIG. 1, or may be performed with a single extraction column 31 wherein the upper stage is the washing portion and the lower stage is the solvent extraction portion as illustrated in FIG. 2. In other words, the present invention provides a process for purification of boric acid wherein the amount of harmful impurities is reduced to an extent that allows the boric acid to be reused in the oxidation reaction, maintains the selectivity of the oxidation reaction at a level of selectivity obtained with fresh boric acid, and virtually eliminates the loss of boric acid in order to cyclically use said boric acid in an oxidation process.

DESCRIPTION OF THE PREFERRED EMBODIMENT

Figure 1:
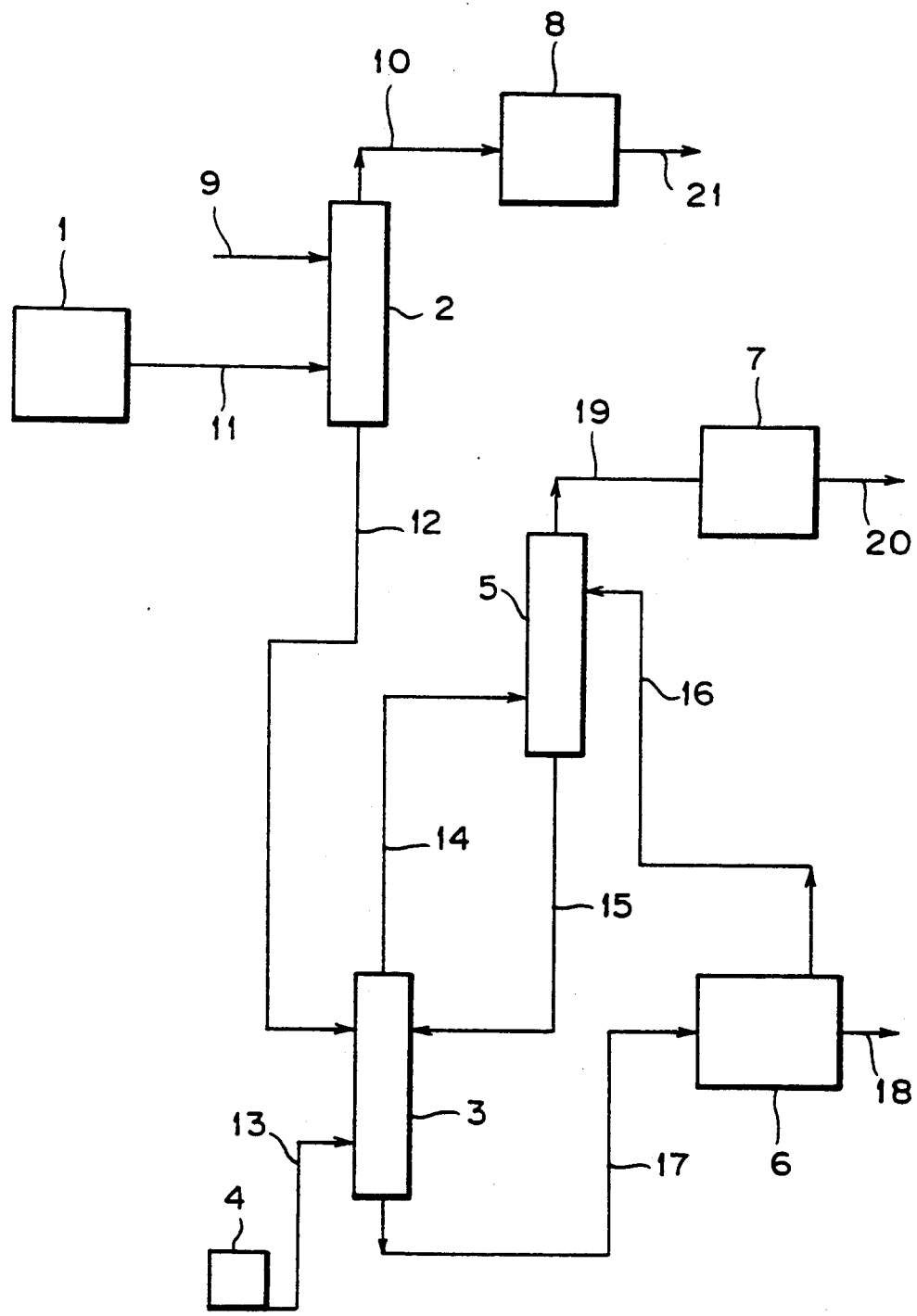
FIG. 1 is an explanatory drawing of the oxidation-catalyzed, solvent extraction purification process.

The following provides a detailed explanation of the present invention.

It is widely known that industrially important oxygenated organic derivatives are formed when hydrocarbons are oxidized with a gas containing molecular oxygen. The boric acid used in this oxidation reaction plays the role of forming a boric acid ester with the target alcohol and preventing high-order oxidation reactions. It is also known to be used as an oxidation assistant that effectively increases the selectivity by which the target monoalcohol or ketone derivatives are converted. In the case of performing said process on an industrial basis, it is necessary to purify the boric acid by isolation and regeneration so that it can be cyclically reused in the oxidation reaction for economic reasons as well.

In the case of cyclododecane for example, the hydrocarbon oxidation reaction of the present invention is carried out under the reaction conditions described to follow. More specifically, the reaction is suitably carried out at a reaction temperature within the range of 140°–200° C., and preferably 150°–180° C. In addition, it is suitably carried out at a reaction pressure within the range of atmospheric pressure to 10 $Kg/cm^2G$, and preferably atmospheric pressure to 5 $Kg/cm^2G$. The oxidation reaction is carried out on cyclododecane by supplying boric acid under the above-mentioned reaction conditions at a suitable oxygen concentration of 2%–50%, and preferably 4%–25%, diluted with air containing molecular oxygen, and/or an inert gas such as nitrogen gas.

In addition, the reaction is carried out under the following reaction conditions in the case of oxidation of cyclohexane. More specifically, the reaction is suitably carried out at a reaction temperature within the range of 140°–200° C., and preferably 150°–180° C. In addition, it is suitably carried out t a reaction pressure within a range of 6–20 $Kg/cm^2G$, and preferably 8–12 $Kg/cm^2G$. The oxidation reaction is carried out on cyclohexane by supplying boric acid under the above-mentioned reaction conditions at a suitable oxygen concentration of 2%–50%, and preferably 4–25%, diluted with air containing molecular oxygen, and/or an inert gas such as nitrogen gas.

As a result of the oxidation reaction, the target alcohol is present in the resulting reaction solution in the form of boric ester. In addition, ketone is formed at a weight ratio of 20:1 to 10:2 with respect to the alcohol. As the boric acid ester of the alcohol contained in the oxidation reaction solution disassociates as alcohol, a hydrolysis reaction is performed by adding water to the oxidation reaction solution.

In order to hydrolyze the boric ester of the alcohol, an amount of water sufficient to dissolve the boric acid is added at a weight ratio of suitably 5%–30%, and preferably 10%–20%, with respect to the oxidation solution. An organic solution containing the target alcohol and ketone to be formed, and unreacted hydrocarbon, as well as aqueous boric acid are obtained. In the case of performing this process industrially, the hydrolysis reaction is performed by bringing the oxidation solution and water in contact by counterflow. Suitable examples of apparatus which perform hydrolysis by counterflow contact include perforated plate column, packed column and rotary disk column types as well as mixer-settler type apparatus. In addition, the operation method is not limited, with either continuous type or batch type able to be used.

When the aqueous boric acid solution obtained by hydrolysis is separated, organic impurities formed as by-products in the oxidation reaction are distributed within the aqueous boric acid solution (examples of which include organic acids such as mono- and dicarboxylic acids, alcohols, hydroxy carboxylic acids and high-order oxidation products). The amount of these organic impurities contained is 2000 ppm to 8000 ppm in terms of total organic carbon (refer to the definition of TOC).

As the above-mentioned organic impurities are contained within the regenerated boric acid obtained by dehydration of aqueous boric acid, when regenerated boric acid is used cyclically in the oxidation reaction, remarkable scaling occurs in the oxidation reaction vessel. As this shortens the operating period, this has a considerably detrimental effect on the ease of operation. In addition, as this also leads to a remarkable decrease in the selectivity and conversion rate to the target alcohol and ketone, the reaction results of the oxidation reaction, the cyclical use of boric acid after removing organic impurities by treating the aqueous boric acid following the oxidation reaction is both necessary and important in order to improve industrial economic feasibility.

Furthermore, the concentration of organic impurities was measured in the form of total organic carbon (TOC) with the Shimadzu TOC-500 Total Organic Carbon Counter. As indicated above, TOC is the abbreviation for Total Organic Carbon.

As the process of the present invention is a method wherein organic impurities in aqueous boric acid are extracted by solvent extraction in order to remove said organic impurities from said aqueous boric acid, selection of the solvent is important. As stated above, the organic impurities in aqueous boric acid solution to be extracted are nearly all polar compounds. If the extraction solvent is a nonpolar solvent as stated previously, it is difficult to satisfactorily remove organic impurities from aqueous boric acid.

Thus, those solvents that can be used industrially are preferably organic solvents that are able to extract the by-products of the above-mentioned oxidation reaction from aqueous solution to the organic solvent as a result of organic impurities being highly soluble in said solvent. Examples of solvents used in the present invention are saturated aliphatic ketones or alicyclic ketones having an oxygen atom and 3-20, and preferably 4-15, carbon atoms within their molecules. In addition, saturated aliphatic or alicyclic alcohols as well as aromatic alcohols having 5-15 carbon atoms can also be used. Moreover, esters similarly having 4-15 carbon atoms can also be used. In other words, the present invention provides a solvent optimum for extracting polar impurities from a strongly polar aqueous solution.

Examples of extraction solvents that satisfy these conditions include hydrocarbon solvents containing ketone groups of saturated aliphatic ketones such as methyl isobutyl ketone, methyl ethyl ketone, methyl isopropyl ketone, methyl propyl ketone, diethyl ketone and methyl butyl ketone; and, alicyclic ketones such as cyclohexanone, methyl cyclohexanone and cyclododecanone; or, methods using mixtures of these solvents.

In addition, examples of alcohols used in the present invention include aliphatic alcohols such as amyl alcohol, isoamyl alcohol, n-hexanol, n-heptyl alcohol, octyl alcohol and capryl alcohol; aromatic alcohols such as benzyl alcohol; and, alicyclic alcohols such as cyclopentanol and cyclohexanol. Examples of esters that are used include formic acid ester, acetic acid ester and propionic acid ester.

As a condition of the extraction process using the above-mentioned solvent of the present invention, the reaction is performed at a solvent ratio within a range of 0.2-4 weight parts solvent to 1 weight part aqueous boric acid solution. The temperature during extraction is within a range of room temperature to 90° C. Examples of extraction apparatus that can be used include a perforated plate extraction column, packed extraction column, mixer-settler extraction apparatus, centrifugal extraction apparatus or rotary disk column.

In addition, as a small amount of boric acid dissolves in the solvent used to extract organic impurities, this is economically disadvantageous if left uncorrected as the boric acid loss will increase. In order to prevent this loss of boric acid, boric acid is extracted by washing the extraction solvent with water. As the water used to extract the boric acid contains a portion of the organic impurities, this is returned to the apparatus which extracts aqueous boric acid solution with solvent. As a result, organic impurities can be removed by extraction from aqueous boric acid while reducing boric acid loss to essentially zero.

The extraction apparatus used for this purpose can be an apparatus in which the above-mentioned solvent extraction portion and water washing portion are divided into two typical extraction columns. In addition, an apparatus may also be used in which counterflow extraction is performed in a single extraction column in which the solvent extraction portion is provided in the bottom of the column and solvent is introduced from the bottom stage of the column while introducing aqueous boric acid following hydrolysis from the intermediate stage of the column. Moreover, this apparatus may also wash the boric acid in the solvent rising in the column and water introduced from the upper stage of the column. A water washing portion may be provided in the top of the extraction apparatus.

The following provides a schematic explanation of an industrial process according to the present invention with reference to the attached drawings.

In FIG. 1, the reaction solution and water are brought in contact by counterflow by introducing an oxidation reaction solution, in which a hydrocarbon such as cyclododecane is reacted with an oxygen-containing gas such as air in the presence of boric acid such as meta-boric acid, from 11 to the bottom portion of hydrolysis column 2 and introducing water from the upper portion 9.

As unreacted hydrocarbon, the target alcohol and ketone along with reaction by-products in the form of impurities are contained in the organic reaction solution from which organic impurities have been extracted by counterflow extraction following hydrolysis of boric ester by water, in order to remove these additional impurities, the quality of the organic phase is attempted to be improved by performing contact treatment with alkali in saponification reaction process 8. Next, as the saponified organic reaction solution contains unreacted hydrocarbon and the target alcohol and ketone, said organic reaction solution is sent to the separation process by 21.

The aqueous solution containing boric acid and organic impurities formed as by-products in the oxidation reaction is introduced from the lower portion of hydrolysis column 2 to the upper portion of solvent extraction column 3. An amount of solvent such as methyl isobutyl ketone required for extraction is introduced from solvent tank 4 to the lower portion of solvent extraction column 3 via 13 where counterflow extraction takes place. As a result, organic impurities in the boric acid are extracted into the solvent after which the solution is discharged via 14 to water washing column 5 where the accompanying boric acid is removed. Consequently, washing is performed by introducing water (using the water separated in 6) via 16. The washing water is taken out via 15 and returned to solvent extraction column 3.

Next, the extraction solvent of water washing column 5 is separated by distillation into extracted impurities and solvent in solvent recovery process 7 after being discharged from washing column 5 via 19. The distillation residue is removed via 7 and suitably processed for disposal. The separated solvent is removed via 20 and returned to solvent tank 4 for cyclical use.

The purified aqueous boric acid, which is the heavy solution of solvent extraction column 3, is removed via 17. In order to remove accompanying solvent, a small amount of which has dissolved in the above-mentioned solution, the aqueous boric acid discharged from solvent extraction column 3 is seam stripped by injection of steam in stripping process 6. This results in the obtaining of purified aqueous boric acid from 18. The separated water removed by the stripping process is removed via 16 and used cyclically for supplying water to water washing column 5.

The extraction purified aqueous boric acid 18 is used in the oxidation reaction after performing suitable dehydration treatment.

Figure 2:
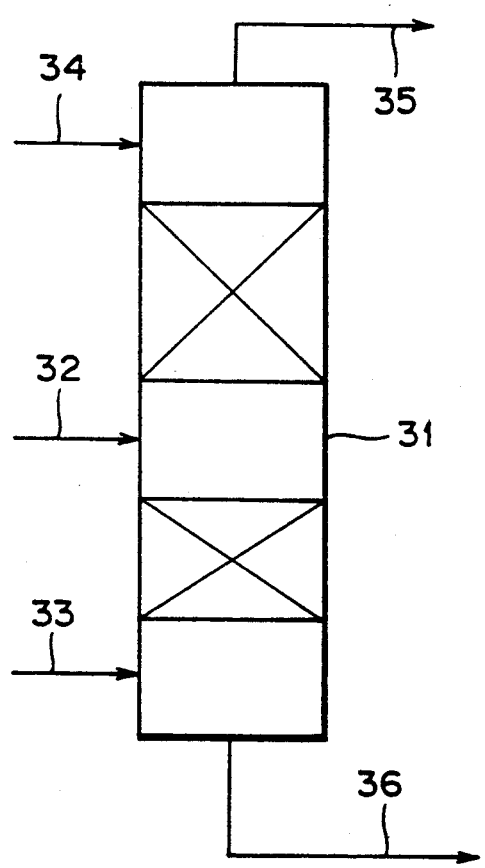
FIG. 2 is an explanatory drawing of an extraction column that simplifies the solvent extraction purification process.

Solvent extraction of the aqueous boric acid, the above-mentioned heavy liquid of hydrolysis, and washing of the extract with water is accomplished by the means indicated in FIG. 2. FIG. 2 indicates an apparatus which simplifies the solvent extraction purification process. The apparatus consists of extraction column 31 in which solvent extraction column 3 and water washing column 5 explained in FIG. 1 are integrated into a single column. The lower portion of this single column is the solvent extraction column while the upper portion is the water washing portion. Thus, this extraction apparatus is able to perform two processes simultaneously. Aqueous boric acid following hydrolysis of the oxidation reaction solution is introduced into the intermediate stage of the column via 32. Counterflow extraction is then performed in the lower solvent extraction portion with solvent 33 introduced into the lower stage of the tower via 33. Organic impurities contained in the aqueous boric acid are thus extracted into the solvent. As a result, purified aqueous boric acid is obtained from the bottom of the extraction column. The aqueous boric acid at this point corresponds to the operation starting at 12 in FIG. 1.

Next, extraction solvent rises from the lower portion and starting at the intermediate stage, counterflow washing is performed in order to wash boric acid accompanying the extraction solvent with water introduced via 34 into the upper stage in the water washing portion of the upper portion. As a result, extraction solvent into which organic impurities have been extracted from aqueous boric acid is discharged from the top of the column. The process after this point corresponds to the operations of 19 and beyond explained in FIG. 1. As such, solvent extraction and water washing of the boric acid accompanying the solvent can be performed simultaneously with a single column in order to simplify solvent extraction.

EXAMPLES

The following provides a detailed explanation of the present invention by indicating reference examples, working examples and comparative examples.

Reference Example 1

300 g of cyclododecane and 140 g of ortho-boric acid ($H_3BO_3$) in the form of an 18% aqueous solution used as an oxidation assistant were charged into 1l autoclave. Removal of free water and dehydration of boric acid were performed while heating and using nitrogen as the water-removing gas. At that time, the exhaust gas is removed outside the system after passing through a condenser mounted on the upper outlet of the autoclave and decompressing to atmospheric pressure via a valve. As the condensate is collected in a water separation tank provided in the lower portion of the condenser thereby separating into an aqueous phase and organic phase, only the organic phase is refluxed to the autoclave. Using a similar operation performed separately, the content of meta-boric acid in the boric acid at this time was 97 mol%. Next, oxidation is performed by introducing air at 2 Kg/cm$^2$G and 170° C. at a flow rate of 0.3 Nl/min. The supply of air is stopped after 90 minutes and returned to atmospheric pressure. The contents of the autoclave are transferred from the autoclave into a flask followed by the addition of 120 g of water and stirring for 10 minutes at 90° C. to perform hydrolysis. After allowing to stand undisturbed, the aqueous boric acid of the heavy solution phase drained from the cock of the bottom portion, said solution phase contained 4600 ppm of organic impurities as total organic carbon (TOC). 50 g of a 10% aqueous NaOH were added to the light solution phase remaining in the flask followed by stirring for 30 minutes to separate after allowing to stand undisturbed. As a result of analysis of the resulting organic phase by gas chromatography, the cyclododecane conversion rate was 17.9%, and the total selectivity of cyclododecanol and cyclododecanone was 86.1%.

Hydrocarbon Conversion Rate (%) =

$$\frac{\text{No. of moles of charged hydrocarbon} - \text{No. of moles of unreacted hydrocarbon}}{\text{No. of moles of charged hydrocarbon}} \times 100$$

Total Selectivity of Corresponding Alcohol and Ketone (%) =

$$\frac{\text{Total no. of moles of alcohol and ketone formed}}{\text{No. of moles of charged hydrocarbon} - \text{No. of moles of unreacted hydrocarbon}} \times 100$$

Comparative Example 1

As a result of performing oxidation according to a procedure similar to Reference Example 1 with the exception of using the aqueous boric acid (TOC: 4600 ppm) obtained in the hydrolysis of Reference Example 1 as the oxidation assistant, the cyclododecane conversion rate was 15.4% and the total selectivity of cyclododecanol and cyclododecanone was 78.2%.

EXAMPLE 1

280 g of methyl isobutyl ketone (abbreviated as MIBK) saturated with water at 80° C. were added to 140 g of aqueous boric acid obtained by hydrolysis in the same manner as Reference Example 1. After extraction by stirring and allowing to stand undisturbed, 280 g of MIBK were again added to the heavy solution followed by extraction. The MIBK phase was separated by allowing to stand undisturbed. Next, 28 g of water were added to the separated heavy solution phase. The 28 g of water along with the dissolved MIBK were distilled by heating after which aqueous boric acid having a TOC of 330 ppm was obtained as the distillate.

The TOC removal rate of this extraction purification was 93%. In addition, although 0.65% of boric acid was dissolved in the MIBK extract, the boric acid concentration in MIBK was lowered to 0.02% by extracting twice with 10 g of water to 100 g of MIBK extract. As a result of performing oxidation similar to Reference Example 1 with the exception of using 140 g of this purified aqueous boric acid for the oxidation assistant, the conversion rate of cyclododecane was 18.4% and the total selectivity of cyclododecanol and cyclododecanone was 86.4%. Thus, results were obtained that are equivalent to those using fresh ortho-boric acid as in Reference Example 1.

Comparative Example 2

With the exception of using 280 g of cyclododecane instead of the MIBK of Working Example 1, extraction was performed twice using a similar method. The TOC concentration of the resulting aqueous boric acid was 2,070 ppm, and the TOC removal rate was 55%. Moreover, as a result of performing oxidation in the same manner as Reference Example 1 with the exception of using this aqueous boric acid for the oxidation assistant, the cyclododecane conversion rate was 16.0% and the total selectivity of cyclododecanol and cyclododecanone was 81.0%.

Reference Example 2

400 g of cyclohexane and 200 g of ortho-boric acid ($H_3BO_3$) in the form of an 18% aqueous solution used as an oxidation agent were charged into 1l autoclave. Removal of free water and dehydration of boric acid were performed while heating and using nitrogen as the water-removing gas. At that time, the exhaust gas is removed outside the system after passing through a condenser mounted on the upper outlet of the autoclave and decompressing to atmospheric pressure via a valve. As the condensate is collected in a water separation tank provided in the lower portion of the condenser thereby separating into an aqueous phase and organic phase, only the organic phase is refluxed to the autoclave. Using a similar operation performed separately, the content of meta-boric acid in the boric acid at this time was 94 mol%.

Next, oxidation is performed by introducing a gas containing 4% oxygen diluted with nitrogen at 9 Kg/cm$^2$G and 165° C. at a flow rate of 1 Nl/min. The supply of gas is stopped after 4 hours after which 170 g of water are added to the autoclave followed by stirring for 10 minutes at 120° C. to perform hydrolysis. After allowing to stand undisturbed, the aqueous boric acid of the heavy solution phase drained from the cock of the bottom portion contained 3500 ppm of organic impurities as total organic carbon (TOC). 50 g of a 10% aqueous NaOH were added to the light solution phase remaining in the flask followed by stirring for 30 minutes to separate after allowing to stand undisturbed. As a result of analysis of the resulting organic phase by gas chromatography, the cyclohexane conversion rate was 10.3%, and the total selectivity of cyclohexanol and cyclohexanone was 86.9%.

Comparative Example 3

As a result of performing oxidation using a procedure similar to Reference Example 2 with the exception of using the aqueous boric acid (TOC: 3500 ppm) obtained in the hydrolysis of Reference Example 2, the conversion rate of cyclohexane was 8.0% and the total selectivity of cyclohexanol and cyclohexanone was 77.9%.

EXAMPLE 2

400 g of methyl isobutyl ketone (abbreviated as MIBK) saturated with water at 80° C. were added to 200 g of aqueous boric acid obtained by hydrolysis in the same manner as Reference Example 2. After extraction by stirring and allowing to stand undisturbed, 400 g of MIBK were again added to the heavy solution followed by extraction. The MIBK phase was separated by allowing to stand undisturbed. Next, 40 g of water were added to the separated heavy solution phase. The 40 g of water along with the dissolved MIBK were distilled by heating after which aqueous boric acid having a TOC of 280 ppm was obtained as the distillate. The TOC removal rate was 92%. As a result of performing oxidation similar to Reference Example 2 with the exception of using 200 g of this purified aqueous boric acid as the oxidation assistant, the conversion rate of cyclohexane was 10.5% and the total selectivity of cyclohexanol and cyclohexanone was 86.8%. Thus, results were obtained that are equivalent to those using fresh ortho-boric acid as in Reference Example 2.

Comparative Example 4

With the exception of using 400 g of cyclohexane instead of the MIBK of Working Example 2, extraction was performed twice using a similar method. The TOC concentration of the resulting aqueous boric acid was 1,790 ppm, and the TOC removal rate was 49%. Moreover, as a result of performing oxidation in the same manner as Reference Example 2 with the exception of using this aqueous boric acid for the oxidation assistant, the cyclohexane conversion rate was 9.4% and the total selectivity of cyclohexanol and cyclohexanone was 81.5%.

EXAMPLE 3

280 g of n-hexanol saturated with water at 80° C. were added to 140 g of aqueous boric acid obtained by hydrolysis in the same manner as Reference Example 1. After extraction by stirring and allowing to stand undisturbed, 280 g of n-hexanol were again added to the heavy solution followed by extraction. The n-hexanol phase was separated by allowing to stand undisturbed. Next, 28 g of water were added to the separated heavy solution phase. The 28 g of water along with the dissolved n-hexanol were distilled by heating after which aqueous boric acid having a TOC of 410 ppm was obtained as the distillate. The TOC removal rate by this n-hexanol extraction purification is 91%.

As a result of performing oxidation similar to Reference Example 1 with the exception of using 140 g of this purified aqueous boric acid as the oxidation assistant, the conversion rate of cyclododecane was 17.5% and the total selectivity of cyclododecanol and cyclododecanone was 85.7%.

EXAMPLE 4

280 g of butyl acetate saturated with water at 80° C. were added to 140 g of aqueous boric acid obtained by hydrolysis in the same manner as Reference Example 1. After extraction by stirring and separation by allowing to stand undisturbed, 280 g of butyl acetate were again added to the heavy solution followed by extraction. The butyl acetate phase was separated by allowing to stand undisturbed. Next, 28 g of water were added to the separated heavy solution phase. The 28 g of water along with the dissolved butyl acetate were distilled by heating after which aqueous boric acid having a TOC of 370 ppm was obtained as the distillate. The TOC removal rate is 92%.

As a result of performing oxidation similar to Reference Example 1 with the exception of using 140 g of this purified aqueous boric acid as the oxidation assistant, the conversion rate of cyclododecane was 17.9% and the total selectivity of cyclododecanol and cyclododecanone was 85.9%.

Effect of the Invention

The present invention has the following advantages:

(1) Organic impurities contained in aqueous boric acid obtained by hydrolysis of an oxidation solution can be removed in a simple apparatus at ambient temperature (25° C.) and atmospheric pressure, the removal rate of said impurities is high, and aqueous boric acid purified by the process of the present invention can be used cyclically in an oxidation process following dehydration treatment without having any effect whatsoever on the reaction.

(2) The recovery rate of boric acid is high and there is essentially no loss.

(3) The purification process of the present invention can also be applied as a process for cycling boric acid to an oxidation process in the case of a simple and superior process which does not require a crystallization procedure wherein aqueous boric acid is dehydrated within the hydrocarbon to be oxidized to form meta-boric acid which is then supplied to the oxidation process together with hydrocarbon, thereby eliminating the complexity of transporting solid state crystals.

In the case of comparing the effect of the process of the present invention with that of the known technology by comparing the removal rates of organic impurities in boric acid for the cyclododecane extraction solvent of the known technology and the methyl isobutyl ketone extraction solvent of the process of the present invention at a solvent ratio of 2, although the removal rate in the case of cyclododecane extraction solvent is 55%, a removal rate of 90% or more is obtained in the case of methyl isobutyl ketone extraction solvent.

Thus, the present invention is carried out to provide an advantageous extraction purification process for removing organic impurities formed as by-products in an oxidation reaction that are contained in circulating aqueous boric acid in order to industrially perform an oxidation reaction in the presence of boric acid. In other words, the present invention provides a process for purification of boric acid which reduces the amount of harmful impurities to an extent that allows circulating aqueous boric acid to be reused in a continuing oxidation reaction, while also maintaining the selectivity of the oxidation reaction at a level of selectivity obtained with fresh boric acid.

We claim:

1. A process for purifying boric acid for hydrocarbon oxidation comprising the steps of:
(A) removing by extraction with an organic polar solvent having at least one oxygen atom in its molecule, organic impurities, formed as by-products of an oxidation reaction, from aqueous boric acid solution obtained by hydrolysis of an oxidation reaction solution, obtained in a hydrocarbon oxidation reaction performed in the presence of boric acid at a temperature of 140° to 200° C., wherein said organic polar solvent is at least one selected from the group consisting of
(a) a saturated aliphatic ketone or an alicyclic ketone having 4 to 15 carbon atoms,
(b) a saturated aliphatic alcohol, an alicyclic alcohol or an aromatic alcohol having 5 to 15 carbon atoms, and
(c) an ester group having 4 to 15 carbon atoms,
(B) regenerating boric acid by removal of free water and dehydration of aqueous boric acid, and
(C) using boric acid cyclically in said oxidation reaction.

2. The method of claim 1 wherein the amount of water at the hydrolysis is 5% to 30% by weight with respect to the oxidation reaction solution.

3. The method of claim 2 wherein the amount of water at the hydrolysis is 10% to 20% by weight with respect to the oxidation reaction solution.

4. The method of claim 1 wherein said organic polar solvent is a saturated aliphatic ketone or an alicyclic ketone having 3 to 20 carbon atoms.

5. The method of claim 4 wherein said organic polar solvent is a saturated aliphatic ketone or an alicyclic ketone having 4 to 15 carbon atoms.

6. The method of claim 1 wherein said organic polar solvent is a saturated aliphatic alcohol, an alicyclic alcohol or an aromatic alcohol having 5 to 15 carbon atoms.

7. The method of claim 1 wherein said organic polar solvent is an ester group having 4 to 15 carbon atoms.

8. The method of claim 4 wherein said saturated aliphatic ketone is at least one selected from the group consisting of methyl isobutyl ketone, methyl ethyl ketone, methyl isopropyl ketone, methyl propyl ketone, diethyl ketone and methyl butyl ketone.

9. The method of claim 4 wherein said alicyclic ketone is at least one selected from the group consisting of cyclohexanone, methyl cyclohexanone and cyclododecanone.

10. The method of claim 6 wherein said aliphatic alcohol is at least one selected from the group consisting of amyl alcohol, isoamyl alcohol, n-hexanol, n-heptyl alcohol, octyl alcohol and capryl alcohol.

11. The method of claim 6 wherein said alicyclic alcohol is cyclopentanol or cyclohexanol.

12. The method of claim 6 wherein said aromatic alcohol is benzyl alcohol.

13. The method of claim 7 wherein said ester group is at least one selected from the group consisting of a formic acid ester, an acetic acid ester and propionic acid ester.

14. The method of claim 1 wherein said organic polar solvent is used in an amount of 0.2 to 4 weight parts with respect to one weight part aqueous boric acid solution.

15. The method of claim 1 wherein the temperature at the extraction is a room temperature to 90° C.

16. The method of claim 1 wherein the aqueous boric acid solution obtained by said extraction is purified by substantially removing a slight amount of the extraction solvent from the aqueous boric acid solution by steam stripping.

17. The method of claim 1 wherein a slight amount of boric acid incorporated into the extracted solution is recovered by back extracting the extracted solution obtained by said extraction with water.

18. The method of claim 1 wherein a mixed solution of the aqueous boric acid solution obtained by said extraction and the hydrocarbon used for an oxidation reaction is prepared, the removal of free water and the dehydration are performed in the mixed solution to regenerate a boric acid, and the hydrocarbon from which water containing the regenerated boric acid has been removed is used for the oxidation reaction.

* * * * *